US007410767B1

(12) United States Patent
Braud et al.

(10) Patent No.: US 7,410,767 B1
(45) Date of Patent: Aug. 12, 2008

(54) HLA-E BINDING

(75) Inventors: Veronique M. Braud, Oxford (GB); David S. J. Allan, Oxford (GB); Graham S. Ogg, Oxford (GB); Christopher A. O'Callaghan, Pasadena, CA (US); Andrew J. McMichael, Beckley (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 09/555,555

(22) PCT Filed: Dec. 4, 1998

(86) PCT No.: PCT/GB98/03686

§ 371 (c)(1), (2), (4) Date: Sep. 25, 2000

(87) PCT Pub. No.: WO99/28748

PCT Pub. Date: Jun. 10, 1999

(30) Foreign Application Priority Data

Dec. 4, 1997 (GB) ................................ 9725764.6

(51) Int. Cl.
*G01N 33/53* (2006.01)
*G01N 33/00* (2006.01)
*C07K 16/28* (2006.01)

(52) U.S. Cl. .................. 435/7.1; 435/7.24; 530/388.22; 530/388.73; 530/389.6

(58) Field of Classification Search ................ 435/7.24, 435/7.1; 530/350, 300, 388.22, 388.73, 389.6
See application file for complete search history.

(56) References Cited

FOREIGN PATENT DOCUMENTS

| | | |
|---|---|---|
| JP | 3112485 | 5/1991 |
| JP | 3112486 | 5/1991 |
| JP | 3112487 | 5/1991 |

OTHER PUBLICATIONS

Braud et al. Nature, 391:795-799, 1998.*

Aldrich et al (1994) Cell 79:649-658.*

Brooks et al. Journal of Immunology (1999) 162:305-313.*

Mingari, MC et al. Int. Immunol. [1995] 7(4):697-703.*

Borrego, Francisco et al.: "Recognition of Human Histocompatibility Leukocyte Antigen (HLA)-E Complexed with HLA Class I Signal Sequence-derived Peptides by CD94/NKG2 Confers Protection from Natural Killer Cell-mediated Lysis" Journal of Experimental Medicine, (Mar. 2, 1998), vol. 187, No. 5, pp. 813-818.

Braud, Veronique M. et al.: "HLA-E Binds to Natural Killer Cell Receptors CD94/NKG2A, B and C" Nature London), (Feb. 19, 1998), vol. 391, No. 6669, pp. 795-799.

O'Callaghan, Christopher et al.: "Structural Features Impose Tight Peptide Binding Specificity in the Nonclassical MHC Molecule HLA-E" Molecular Cell, (Mar. 1998), vol. 1, No. 4, pp. 531-541.

Leibson, Paul J.: "Cytotoxic Lymphocyte Recognition of HLA-E: Utilizing a Nonclassical Window to Peer into Classical MHC" Immunity, (Sep. 1998), vol. 9, No. 3, pp. 289-294.

Posch et al.: "HLA-E is the Ligand for the Natural Killer Cell CD94/NKG2 Receptors" Journal of Biomedical Science, (Sep. 1998), vol. 5, No. 5, pp. 321-331.

Llano, M. et al.: "HLA-E Bound Peptides Influence Recognition by Inhibitory and Triggering CD94/NKG2 Receptors: Preferential Response to an HLA-G-Derived Nonamer" Eur. J. Immunol. (Sep. 1998), vol. 28, No. 9, pp. 2854-2863.

O'Callaghan, Christopher et al.: "Structure and Function of the Human MHC Class Ib Molecules HLA-E, HLA-F and HLA-G" Immunol. Rev., (1998), vol. 163, pp. 129-138.

Aramburu et al., "A Novel Functional Cell Surface Dimer (Kp43) Expressed By Natural Killer Cells And T Cell Receptor $\gamma/\delta^+$ Lymphocytes," The Journal of Immunology, vol. 144, No. 8, pp. 3238-3247 (1990).

Houchins et al., "DNA Sequence Analysis of NKG2, a Family of Related cDNA Clones Encloding Type II Integral Membrane Proteins on Human Natural Killer Cells," J. Exp. Med., vol. 173, pp. 1017-1020 (Apr. 1991).

Ulbrecht et al., "The HLA-E Gene Encodes Two Differently Regulated Transcripts And A Cell Surface Protein," The Journal Of Immunology, vol. 149, No. 9, pp. 2945-2953 (1992).

Ulbrecht et. al., "Impaired Intracellular Transport and Cell Surface Expression of Nonpolymorphic HLA-E: Evidence for Inefficient Peptide Building," J Exp Med, vol. 176, pp. 1083-1090 (1992).

Shawar et al., "Antigen Presentation By Major Histocompatibility Complex Class I-B Molecules," Annual Review of Immunology, vol. 12, pp. 839-880 (1994).

Pérez-Villar, et al, "Functional Ambivalence of the Kp43 (CD 94) NK Cell-Associated Surface Antigen," The Journal of Immunology, vol. 154, pp. 5779-5788 (1995).

Phillips et al., "CD94 and a Novel Associated Protein (94AP) Form a NK Cell Receptor Involved in the Recognition of HLA-A, HLA-B, and HLA-C Allotypes," Immunity, vol. 5, pp. 163-172 (1996).

Lazetic et al., "Human Natural Killer Cell Receptors Involved in MHC Class I Recognition Are Disulfide-Linked Heterodimers of CD94 and NKG2 Subunits," The Journal of Immunology, vol. 157, pp. 4741-4745 (1996).

(Continued)

*Primary Examiner*—David A. Saunders
*Assistant Examiner*—F. Pierre VanderVegt
(74) *Attorney, Agent, or Firm*—Volpe and Koenig, P.C.

(57) ABSTRACT

The invention relates to a method of testing a compound for biological activity, which method comprises providing cells expressing one of the CD94/NKG2 family of receptors, contacting the cells with recombinant HLA-E under binding conditions in the presence of the test compound, and determining whether the presence of the compound affects the binding of HLA-E to the cells. The HLA-E property of binding to CD94/NKG2 receptors on NK cells and a subset of CD8+ T cells is useful for targeting CD94/NKG2+ cells for a variety of purposes such as identification, isolation, killing or inactivation.

22 Claims, 4 Drawing Sheets

OTHER PUBLICATIONS

Sivori et al., "CD94 functions as a natural killer cell inhibitory receptor for different HLA class I alleles: identification of the inhibitory form of CD94 by the use of novel monoclonal antibodies," Eur. J. Immunol., vol. 26, pp. 2487-2492 (1996).

Sivori et al., "Inhibitory CD94 Molecules Identified by the Z199 Monoclonal Antibody Recognize Different HLA-Class I Molecules," Transplantation Proceedings, vol. 28, No. 6, pp. 3199-3203 (1996).

Carretero et al., "The CD94 and NKG-2-A C-type lectins covalently assemble to form a natural killer cell inhibitory receptor for HLA clss I molecules," Eur. Journal of Immunology, vol. 27, pp. 563-567 (1997).

Houchins et al., "Natural Killer Cell Cytolytic Activity Is Inhibited by NKG2-A and Activated by NKG2-C," The Journal of Immunology, vol. 158, pp. 3603-3609 (1997).

Braud et al., "The human major histocompatibility complex class Ib molecule HLA-E binds signal sequence-derived peptides with primary anchor residues at position 2 and 9," Eur. J. Immunol., vol. 27, pp. 1164-1169 (1997).

Plougastel et al., "Cloning of *NKG2-F*, a new member of the *NKG2* family of human natural killer cell receptor genes," Eur. J. Immunol., vol. 27, pp. 2835-2839 (1997).

Lanier et al., "Arousal and inhibition of human NK cells," Immunological Reviews, Vo. 155, pp. 145-154 (1997).

Braud et al., "TAP- and tapasin-dependent HLA-E surface expression correlates with the binding of an MHC class I leader peptide," Current Biology, vol. 8, No. 1, pp. 1-10 (1998).

Braud et al., "HLA-E binds to natural killer cell receptors CD 94/NKG2A, B and C," Nature, vol. 391, pp. 795-799 (1998).

Lee et al., "HLA-E Surface Expression Depends on Binding of TAP-Dependent Peptides Derived from Certain HLA Class I Signal Sequences," The Journal of Immunology, vol. 160, pp. 4951-4960 (1998).

Lanier et al., "Immunoreceptor DAP12 bearing a tyrosine-based activation motif is involved in activating NK cells," Nature, vol. 391, pp. 703-707 (1998).

* cited by examiner

SEQUENCE LISTING

```
<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: peptides
      generated from MHC leader sequences

<400> SEQUENCE: 1

Val Met Ala Pro Arg Thr Leu Val Leu
  1               5


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: peptides
      generated from MHC leader sequences

<400> SEQUENCE: 2

Val Met Ala Pro Arg Thr Leu Leu Leu
  1               5


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: peptides
      generated from MHC leader sequences

<400> SEQUENCE: 3

Val Met Ala Pro Arg Thr Val Leu Leu
  1               5


<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: peptides
      generated from MHC leader sequences

<400> SEQUENCE: 4

Val Met Ala Pro Arg Thr Leu Ile Leu
  1               5


<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: peptides
```

-continued generated from MHC leader sequences

<400> SEQUENCE: 5

Val Met Ala Pro Arg Thr Leu Phe Leu
1 5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: peptides generated from MHC leader sequences

<400> SEQUENCE: 6

Val Met Gly Pro Arg Thr Leu Val Leu
1 5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: peptides generated from MHC leader sequences

<400> SEQUENCE: 7

Val Thr Ala Pro Arg Thr Val Leu Leu
1 5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: peptides generated from MHC leader sequences

<400> SEQUENCE: 8

Val Thr Ala Pro Arg Thr Leu Leu Leu
1 5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: peptides generated from MHC leader sequences

<400> SEQUENCE: 9

Val Met Pro Pro Arg Thr Leu Leu Leu
1 5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: peptides generated from MHC leader sequences

<400> SEQUENCE: 10

Val Met Glu Pro Arg Thr Leu Ile Leu
1 5

<210> SEQ ID NO 11

-continued

```
<211> LENGTH: 9
<212> TYPE: PRT
<213> ORGANISM: Artificial Sequence
<220> FEATURE:
<223> OTHER INFORMATION: Description of Artificial Sequence: peptides
      generated from MHC leader sequences

<400> SEQUENCE: 11

Val Met Ala Pro Arg Ala Leu Leu Leu
  1               5


<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 12

gtgggctaag cttacggctt ccatctcagg gtgacgggct c                         41


<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 13

ctacgggcat atggtagatg gaaccctcct tttactctcc                           40


<210> SEQ ID NO 14
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 14

ccgtacctcg agcatatggg ttctcattct ttaaaatatt ttcatacttc tgtatctaga     60

cccggccg                                                              68


<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 15

tggtgtctag aggatcctgg cttccatctc agggtgacgg gctcg                     45


<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16

gcgtctagaa tggtggtcat ggcaccccga                                      30


<210> SEQ ID NO 17
<211> LENGTH: 30
<212> TYPE: DNA
<213> ORGANISM: Artificial Sequence
```

-continued

<220> FEATURE:
<223> OTHER INFORMATION: Description of Artificial Sequence: Primer

<400> SEQUENCE: 17
catggagtgg gagccggccc aggtctcggt 30

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
ggctcccact ccatgaggta t 21

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 19
aagctttcaa gctgtgagag aca 23

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
accgagacct gggccgttga tgaacaactg 30

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 21
gcaagcttct aaaggaagac ggtctgttc 29

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 22
gggcgtcgac ccggactcag aatctcctca gacgccgag 39

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 23
cagttgttca tcaacggccc aggtctcggt 30

-continued

```
<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 24

ctcggcggcc ctggccctga ccgagacctg ggcgggctcc cactccttg              49


<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 25

ttctgtctag attacaagct gtgagactca gacccctg                          38


<210> SEQ ID NO 26
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 26

ctgaccgaat tcgccgccac catgctggtc atggcgcccc gaaccgtcct cctgctgctc   60

tcggcggccc tggcc                                                    75
```

HLA-E BINDING

This invention relates to methods of identifying, targeting and of isolating a group of CD94+ cells, in particular a group of CD94+ cells including natural killer (NK) cells and a subset of T cells. The invention also relates to methods of targeting functional moieties such as toxins to the CD94+ cells. The invention further relates to multimeric complexes of HLA-E for use in the methods.

Human leukocyte antigen-E (HLA-E) is a nonclassical MHC class Ib molecule of very limited polymorphism. Human nonclassical MHC class Ib molecules (which include HLA-E, HLA-F and HLA-G) are homologous to classical MHC class Ia molecules (HLA-A, HLA-B and HLA-C) but are characterised by limited polymorphism and low cell surface expression (reviewed in Shawar et al 1994 *Annu. Rev. Immunol.* 12: 839). The mouse MHC class Ib molecule Qa-1 shares some characteristics with HLA-E in that it displays a broad tissue distribution and some structural similarities in the peptide-binding groove (reviewed in Soloski et al 1995 *Immunol. Rev.* 147: 67).

Whereas the function of the classical MHC class I molecules in presenting peptides derived from cytosolic proteins to CD8+ T cells is well-established, the function of nonclassical MHC molecules remains unknown, in particular for HLA-E. HLA-E is transcribed in most tissues. Recently, we have shown that HLA-E is able to bind in its peptide-binding site peptides derived from MHC class I leader sequences at positions 3 to 11 (Braud et al 1997 *Eur. J. Immunol.* 27: 1164-1169). The optimum binding peptide is a nonamer. Using alanine and glycine substitutions, it was established that there are primary anchor residues at positions 2 and 9 of the peptide and secondary anchor residues at position 7 and possibly position 3. The literature suggests that HLA-E is localised in the endoplasmic reticulum (ER) and might have a role in the loading of peptides onto classical MHC class I molecules in a similar way to HLA-DM for MHC class II molecules. Neither mouse cells transfected with HLA-E and human β2 microglobulin (β2m) nor the 721.221 cell line which only expresses HLA-E and HLA-F, show surface expression of HLA-E (Ulbrecht et al, *J. Immunol.* 1992 149: 2945-2953 and *J. Exp. Med.* 1992 176: 1083-1090).

Assembly of MHC class I molecules occurs in the endoplasmic reticulum (ER) and requires peptide translocation through the transporter associated with antigen processing (TAP) (reviewed in Cerundolo et al 1996 In *HLA and MHC genes, molecules and function*, Edited by Browning M, McMichael A. Oxford: Bios. Scientific Publisher Ltd; 193-223). In human cells, newly synthesised MHC class I heavy chains associate with calnexin which is later displaced by the association of β2m. Following dissociation of calnexin, class I-β2m heterodimers are stably associated with another ER resident protein, calreticulin. Another molecule, tapasin, which is associated with TAP and with MHC class I-calreticulin complexes, acts as a bridge between them. MHC class I association with TAP facilitates peptide binding and the class I molecules are released and exported to the cell surface upon stable loading of peptide.

Natural killer (NK) cells are cytotoxic cells which have the morphology of large granular lymphocytes and are normally defined by their activity. They use recognition systems which are not yet clearly understood. Recognition of tumour cell lines and virally-infected cells is however driven by the absence of MHC class I at the target cell surface (some MHC class I molecules interact with specific NK receptors). NK cell cytotoxicity is mediated by the interaction between Fas and Fas ligand or by the release of the contents of the intracellular granules including the pore forming protein perforin and the serine protease granzyme B. NK cells are generally but not exclusively CD3− and CD56+. They may also be CD16+ and some are also CD8+. Certain CD8+ T cells have an NK cell-like function, in that they are able to kill MHC class I negative cells.

NK cells express receptors that interact with MHC class I and serve to inhibit or activate NK cell-mediated cytotoxicity. The killer cell immunoglobulin-like receptors (KIR), which are members of the immunoglobulin superfamily, make up one such group of receptors.

Another NK cell inhibitory receptor which has a similar effect is the CD94/NKG2A receptor from the C-type lectin superfamily, which is expressed at the cell surface as a heterodimer of CD94 covalently associated with NKG2A. CD94 also associates with other members of the NKG2 family, which consists of four closely related molecules NKG2A, B, C and E and two more distantly related molecules NKG2D and F. CD94/NKG2A and B are both inhibitory NK cell receptors which interact with MHC class I to inhibit NK cell lysis, while CD94/NKG2C is a stimulatory NK cell receptor which interacts with MHC class I to perform an NK cell triggering function.

The CD94/NKG2C activator receptor contains a third subunit DAP12, which is expressed as a disulphide-bonded homodimer and interacts with NKG2C via charged residues in the transmembrane domains (Lanier, 1998, *Nature* 391: 703; Lanier et al, 1998, *Immunity* 8:693). DAP12 is necessary for efficient transport of the CD94/NKG2C complex to the cell surface. Ligation of CD94 on CD94/NKG2C/DAP12 transfectants causes tyrosine phosphorylation of DAP12, suggesting that it induces cellular activation via DAP12.

Four genes encode the NKG2 glycoproteins: NKG2A, NKG2C, NKG2E and NKG2D/F (Houchins et al, 1991, *J. Exp. Med.* 173: 1017; Plougastel et al, 1997, *Eur. J. Immunol.* 27: 2835). NKG2A and B are alternative splicing products (differing by an 18 amino acid segment immediately outside the transmembrane region). NKG2C is highly homologous to NKG2A and B with 94% homology in the external C terminal domain and 56% homology through the internal and transmembrane regions. NKG2D is distantly but significantly related (21% homology) as too is NKG2F.

It has recently been discovered that HLA-E is stably expressed at a low level on the surface of cells. Its expression at the surface correlates with co-expression of human MHC class I molecules which possess a peptide in their leader sequence capable of binding to HLA-E. Loading of these signal sequence-derived peptides is TAP and Tapasin-dependent and HLA-E assembly appears to be similar to classical MHC class I assembly (Braud et al 1998 *Current Biology* 8:1-10).

It has now also been discovered that HLA-E binds to NK cells expressing receptors CD94/NKG2A, B and C. The majority of NK cells express CD94/NKG2 receptors and the majority of NK cells are capable of binding HLA-E. HLA-E also binds to a small subset of T cells expressing CD94/NKG2 heterodimers.

Furthermore, surface expression of HLA-E provides protection against killing by CD94/NKG2A+ NK cells.

In addition, it has been discovered that multimeric HLA-E molecules bind strongly to NK cells and the T cell subset expressing CD94/NKG2.

In its broadest sense, the invention provides the use of the interaction between HLA-E and NK cells and/or a subset of T cells, to identify and/or target and/or isolate those cells; and HLA-E in a suitable form for such use.

The invention provides in one aspect a method of causing an interaction of CD94/NKG2+ cells, which method comprises contacting the cells with HLA-E under binding conditions.

The invention thus encompasses in one embodiment a method of identifying the presence of CD94/NKG2+ NK cells and T cells in a sample, which method comprises contacting the sample with HLA-E under suitable binding conditions and detecting binding of HLA-E to the cells.

In another embodiment, the method according to the invention provides a method of selecting for CD94/NKG2+ cells, in particular NK cells and a subset of T cells, from a sample, which method comprises contacting the sample with HLA-E under binding conditions and separating cells bound to the HLA-E from the mixture.

In still another embodiment there is provided a method of killing or inactivating NK cells and a subset of T cells, which method comprises contacting the cells with HLA-E under binding conditions and carrying out targeted killing on the bound cells. Any targeted killing method may be used, for example NK cells may be identified by detecting bound HLA-E, and then destroyed by use of a laser, or the HLA-E may carry a toxic moiety which kills or inactivates the cells to which the HLA-E binds.

In yet another embodiment, the invention provides a method of modifying NK cell activity against a potential target cell, by expressing HLA-E at the surface of the target cell. In this embodiment, the binding of the CD94/NKG2 receptors to the cell surface HLA-E thus causes an interaction between the CD94/NKG2+ cells and the HLA-E bearing cells. In the case of CD94/NKG2A or B receptors, this will be an inhibitory interaction the effect of which is to protect the HLA-E bearing cell from killing by the NK cells. In the case of CD94/NKG2C receptors there may be an NK cell stimulatory effect. In the case of NK cells expressing both inhibitory and activator CD94/NKG2 receptors, the overall effect of an interaction with HLA-E at the target cell surface is an inhibitory one, since the inhibitory receptors override the stimulatory receptors.

Thus, the invention involves the use of the newly discovered HLA-E—CD94/NKG2 receptor binding partnership for a variety of possible purposes. The interaction in the method according to the invention may be simply the binding of the CD94/NKG2 receptors to the HLA-E. Alternatively or additionally the interaction of the CD94/NKG2+ cells with the HLA-E may give rise to an effect on the activity of the CD94/NKG2+ cells, such as an inhibitory effect.

In further aspects, the invention provides CD94/NKG2+ cells isolated by the method according to the invention; and a population of cells depleted of CD94/NKG2+ cells by the method according to the invention.

In another aspect the invention provides a non-human mammalian cell which expresses HLA-E at the cell surface by virtue of a nucleic acid encoding HLA-E integrated into the genome of the cell. The nucleic acid encoding HLA-E is a heterologous nucleic acid in the sense that it is not found in those cells in nature. The invention also provides recombinant animals comprising such cells, which animals include transgenic animals which contain HLA-E-encoding nucleic acid material in their somatic and germ cells, as well as animals which are recipients of a transplant from such transgenic animals.

In another aspect the invention provides a method of testing a compound for biological activity, which method comprises:

(i) providing cells expressing CD94/NKG2 receptors at the cell surface;

(ii) contacting the cells with HLA-E in the presence of the test compound; and (iii) determining whether the presence of the compound affects the binding of HLA-E to the cells; and compounds identified by the method as being compounds which affect the binding of HLA-E to CD94/NKG2 receptors.

Preferably the cells expressing CD94/NKG2 receptors in the method according to this aspect of the invention do not naturally express the receptors, and most preferably they are non-human cells. The cells are preferably stable transfectants, that is to say they contain nucleic acid material expressing CD94/NKG2 stably integrated into their genome.

Compounds such as antibodies, in particular monoclonal antibodies, may be screened by the method for a particular desired property. Compounds may be identified by the method which interfere specifically with the interaction between HLA-E and CD94/NKG2A but not CD94/NKG2C, or vice versa. Antibodies with such specificity will be useful, for example to enable CD94/NKG2A NK cells to be distinguished from CD94/NKG2C cells. Therapeutic uses for antibodies which inhibit the binding of HLA-E to CD94/NKG2 receptors are also envisaged, for example in bone marrow transplantation. It can be difficult to find a matched human donor and allogeneic cells might not possess MHC class I ligands that can engage the inhibitory receptors of all NK cells. An antibody which specifically blocks the binding of NK cells to the activator receptor CD94/NKG2C will therefore be useful. Another example of a possible therapeutic use of the antibodies is in the treatment of certain autoimmune diseases.

In another aspect the invention provides a multimer of HLA-E comprising two or more HLA-E molecules, said multimer having enhanced binding capability compared to non-multimeric HLA-E, optionally labelled with a signal moiety. The multimers of HLA-E contain at least two subunits which have the binding properties of HLA-E receptors (that is they bind CD94/NKG2 receptors), linked together to produce a bifunctional or multifunctional species. Each subunit comprises all or a substantial part of the extracellular region of HLA-E, generally at least the $\alpha 1$, $\alpha 2$ and $\alpha 3$ HLA-E domains, together with $\beta 2$ microglobulin, and a suitable peptide in the peptide binding groove. Preferred HLA-E multimers are tetramers, but other multimers for example dimers, trimers and multimers containing 5, 6, 7 etc. HLA-E molecules are not excluded.

In another aspect the invention provides a recombinant HLA-E coupled to a toxic agent. The purpose of the toxic agent is to kill or inactivate cells to which the recombinant HLA-E binds. It is sufficiently toxic for that purpose. The toxic agent preferably has a localised effect, that is it preferably does not affect surrounding cells to which the HLA-E is not bound. Preferably the recombinant HLA-E is in the form of a multimer.

BRIEF DESCRIPTION OF THE DRAWINGS

In FIG. 2A, peripheral blood lymphocytes from normal donor SRJ stained with the anti-CD94 antibody HP3D9 (1/50 dilution of ascites) followed by FITC-anti-mouse IgG $(Fab')_2$ (Sigma); HLA-E tetramer PE alone; or HLA-E tetramer-PE in the presence of HP3D9 (1150) which inhibited HLA-E tetramer staining. In FIG. 2B, the NK cell line NKL expressing the NK receptor CD94/NKG2A but none of the KIR molecules stained with the anti-CD94 antibody DX22 (1 mg) followed by PE-anti-mouse IgG; HLA-E tetramer-PE; or HLA-E tetramer-PE in the presence of 1 mg of DX22 antibody which inhibited HLA-E tetramer staining. Percentages in each quadrant are listed in the upper right.

FIG. 3A illustrates P815 cells stably transfected with pBJ-neo vector containing human CD94 cDNA or NKG2B cDNA. Cells were stained with PE-control mouse IgG1 (cMIgG1) or IgG2b (cMIgG2b), anti-CD94 antibody DX22-PE, anti-NKG2A and B antibody DX20-PE, or HLA-E tetramer-PE. FIG. 3B illustrates 293T cells stably transfected with CD94 were transiently transfected with NKG2A, NKG2B, and NKG2C. Flow cytometry staining was performed using rabbit preimmune serum (cRIgG) 1/500 final dilution or rabbit anti-CD94/NKG2 heterodimer serum (anti-CD94/NKG2) 1/500 final dilution, both followed by FITC-anti-rabbit IgG, or with HLA-E tetramer-PE.

In FIG. 4A, lysis of 721.221 cells expressing HLA-B*5801, HLA-G or a chimeric molecule (GLS-B*5801) containing the HLA-G leader sequence and the extracellular, transmembrane, and cytoplasmic domains of HLA-B*5801 by a representative NK-cell clone expressing the CD94/NKG2A receptor. Assays were performed at an effector to target ratio of 0.5:1, in the presence of control immunoglobulin (cIg), anti-CD94 (DX22), or anti-HLA class I (DX17) at 5 $\mu g\ ml^{-1}$. In FIG. 4B, lysis of 721.221 cells expressing mouse CD80 or a chimeric molecule (B7LS-mCD80) containing the HLA-B*0702 leader sequence and the extracellular, transmembrane, and cytoplasmic domains of mouse CD80 by two representative NK-cell clones expressing the CD94/NKG2A receptor. Assays were performed at an effector-to-target ratio of 1:1 in the presence of control immunoglobulin (cIg) or anti-CD94 (DX22) at 10 $\mu g\ ml^{-1}$.

DETAILED DESCRIPTION OF THE PREFERRED EMBODIMENTS

Figure 1:
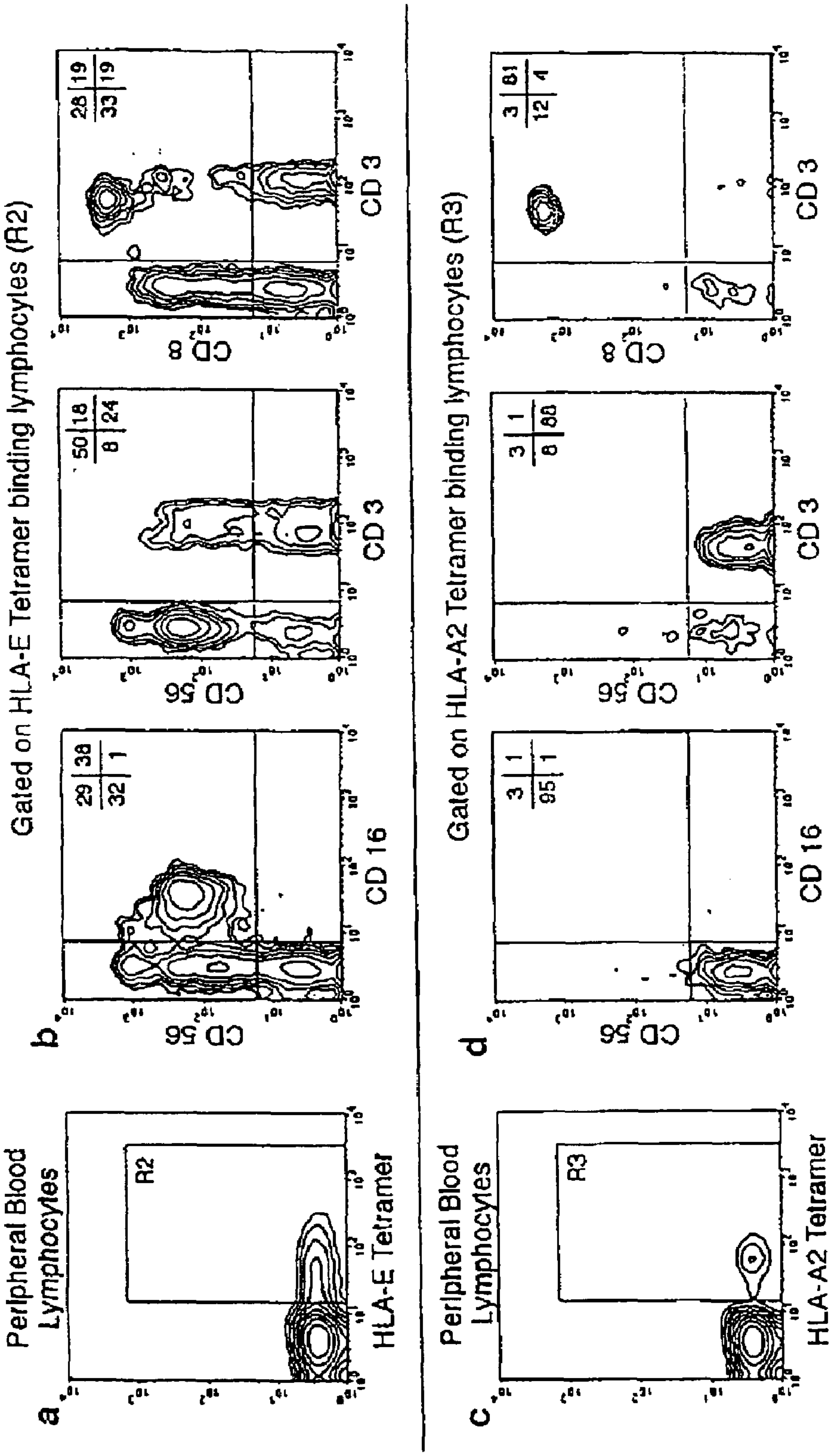
FIG. 1 illustrates a series of graphs showing HLA-E tetramer binds NK cells and a subset of T cells. Flow cytometry analysis on gated peripheral blood lymphocytes from normal EBV seropositive donor VB using (FIG. 1A) HLA-E tetramer refolded around the leader sequence peptide residues 3-11 from HLA-B*0801 or (FIG. 1C) HLA-A2 tetramer refolded around the Epstein Barr Virus (EBV) lytic cycle BMLF1 259-267 peptide epitope. The phenotypes of (FIG. 1B) HLA-E tetramer or (FIG. 1D) HLA-A2 tetramer binding lymphocytes were further investigated in triple color stains as indicated. Percentages in each quadrant are represented by the cross in the upper right.

The invention is useful for diagnostic purposes and in general for monitoring diseases. Detection and/or quantitation of NK cells or a sub-population of NK cells, or a sub-population of T cells (which may be further identified by co-staining with anti-CD8 or anti-CD4 antibody or antibodies or ligands to other T cell markers) will be useful in a variety of conditions, including the following:

(i) Cancer, Lymphomas and Leukaemias (Particularly Large Granular Cell Leukaemias).

NK cells are believed to have an anti-tumour cell activity. A marker for progress of therapy, or simple prognosis, can be provided by monitoring NK cell numbers and optionally their state of activation. This will provide an extremely simple test. The methods described herein can be used to determine or estimate NK cell numbers in a sample taken from a patient. The numbers of NK cells and T cells with an NK-like activity (CD94/NKG2+) can be estimated by the use of antibodies against markers of NK cells (eg CD56 or CD16) or antibodies against T cell markers (eg CD3). The state of activation of the NK cells can be investigated by co-staining with antibodies to activation markers. Alternatively, the activation state of NK cells can be assessed in a functional assay in vitro. The NK cells are isolated from the sample and their cytolytic activity and/or ability to produce cytokines (eg interferon-γ and/or TNF-α) is assessed, either directly or after a short period in culture.

(ii) Infections

NK cell numbers may change during viral or other infections and knowing their numbers could be of great value for example in HIV infected patients. It will be of particular interest to monitor NK cell numbers in cytomegalovirus (CMV) infections. CMV has sequences in its proteins that are capable of affecting HLA-E expression. More specifically, these CMV sequences induce cell surface expression of HLA-E in the virus host cell.

(iii) Pregnancy

There is interest in the role of NK cells in the placenta, in the prevention of rejection of the foetus. The invention provides a means to monitor NK cells in the placenta.

(iv) Transplantation

NK cells may be involved in transplant rejection and graft-versus-host disease (GVHD) after bone marrow transplantation. Monitoring of NK cells may be of value in patient management.

(v) Immunodeficiency

The diagnostic use of HLA-E can be extended to the detection of new immunodeficiency syndromes, either inherited or acquired, which exhibit lower or higher than normal NK cell levels. Some treatments may be toxic or stimulatory to NK cells.

(vi) Autoimmune Diseases

It will be useful to monitor NK cells in autoimmune diseases such as systemic lupus erythematosus, diabetes, thyroid diseases, vitiligo, rheumatoid arthritis etc.

(vii) Following Treatment

The invention also enables the monitoring of secondary effects of any treatment which could lead to up or downregulation of CD94/NKG2+ NK cells.

Although NK cells are specifically referred to in the examples of diseases and conditions above, monitoring of the T cell subset expressing receptors recognised by HLA-E is also included.

The invention also has a range of therapeutic applications. Examples Include the Following (i) Enhancing NK Levels The invention provides a method of selecting HLA-E binding NK cells or T cells from a mixed cell population. The selected cells can be expanded in vitro and returned to the patient. Such treatment may be effective in some serious infections or cancers where a growth deficiency of these cells is associated with poor prognosis.

(ii) Removing NK Cells

The invention provides methods and means for removal of HLA-E binding NK cells and T cells, for example from bone marrow to be used as donor bone marrow in transplantation.

T cell depletion of bone marrow using other techniques is already known and is effective. HLA-E coupled to a toxin could also be used to destroy HLA-E binding cells in vivo.

(iii) Expressing HLA-E at the Surface of Cells

The invention provides a method and means for inhibiting or stimulating NK cell activity, by providing HLA-E at the surface of cells. NK cells play a role in transplant rejection. Therefore, by ensuring that HLA-E is expressed at the cell surface in a xenotransplant organ or tissue, the likelihood of rejection will be reduced and rejection may be avoided altogether.

Multimers of HLA-E in accordance with the invention can take a variety of possible forms. The HLA-E molecules may be associated with one another via a linker molecule. Alternatively or additionally the HLA-E molecules may be attached to larger entities such as membrane structures, for example liposomes. Suitable linker molecules include multivalent attachment molecules such as avidin, streptavidin and extravidin each of which has four binding sites for biotin. Thus, biotinylated HLA-E molecules can be formed into multimer complexes of HLA-E having up to four HLA-E binding sites. The number of HLA-E molecules in the resulting complex will depend upon the ratio of HLA-E molecules to linker molecules used to make the complexes, and also on the presence or absence of any other biotinylated molecules such as biotinylated signal moieties or toxic moieties. Preferred complexes are trimeric or tetrameric HLA-E complexes.

Other cross-linking techniques suitable for preparing HLA-E dimers or multimers include, for example, antibody cross-linking to produce dimers, and techniques using cross-linking agents such as fluorogenic compounds or other chemical cross-linking agents.

Described herein in detail is a method of making HLA-E tetramers by biotinylating recombinant HLA-E heavy chains $\alpha 1$, $\alpha 2$ and $\alpha 3$ domains) and constructing complexes by refolding the HLA-E heavy chains in vitro with $\beta 2$m molecules and with a synthetic leader peptide from HLA-B. In the method described, biotinylation sites are engineered into the C terminus of the HLA-E heavy chain and the recombinant HLA-E molecules are biotinylated by means of a suitable biotinylating enzyme. The multivalent linker molecule, in this case extravidin, is then added. Variations of this tetramerisation method are envisaged. For example, the $\beta 2$m could be chemically biotinylated at its seven lysine residues, four of which are in an appropriate position to allow complexing.

Whatever form of HLA-E is used, a suitable peptide for binding in the HLA-E peptide groove will be required. Tables 1 and 2 show examples of possible peptides found at residues 3 to 11 of MHC class I leader sequences. The tables indicate which of these are found to bind to HLA-E in vitro. Other peptides which bind to HLA-E may be used, for example peptides from viral proteins which may be the same as or different to MHC class I leader sequence peptides. Although nonamer peptides are usually the optimum size for binding to HLA-E, it is possible that peptides which are slightly shorter or slightly longer, e.g. by one or two residues at one or both ends, will also work. A suitable assay for identifying synthetic peptides which bind to HLA-E is described in Braud et al 1997 *Eur. J. Immunol.* 27:1164-1169.

Labelling of the HLA-E may be carried out by any suitable method. Described herein is tetrameric HLA-E labelled with phycoerythrin via the extravidin used to form the tetrameric complex. A variety of other signal moieties may be employed at a variety of possible sites on the HLA-E monomer or multimer, and the HLA-E may be labelled before, during or after multimerisation. Useful signal moieties commonly employed for labelling proteins include radioactive (e.g. 32-P or 33-P or 35-S), fluorescent (e.g. FITC) and enzymatic (e.g. horseradish peroxidase) labels. These and other detectable labels may be employed in the invention.

HLA-E is also provided according to the invention linked to a support. The HLA-E thus immobilised is particularly useful for capture purposes, that is for capturing and separating CD94/NKG2+ cells. A mixture containing or suspected of containing CD94/NKG2+ cells is brought into contact with the immobilised HLA-E under binding conditions and unbound material is removed. CD94/NKG2+ cells may then be recovered. Examples of suitable solid supports include but are not limited to support bodies or particles which may be for example in the form of beads, wells, tubes and plates. The HLA-E may be immobilised by a variety of means well-known in the art and may be attached to the support by means of a suitable linker molecule.

HLA-E is also provided according to the invention attached to an effector agent such as a toxic moiety, the purpose of which may be the targeted depletion of CD94/NKG2+ cells in a mixed population of cells in vitro or in vivo. The toxic moiety is preferably a toxin which selectively kills the cells to which the HLA-E is bound. Suitable toxins can be derived from natural sources such as plants (for example ricin, abrin) or bacteria (for example diphtheria toxin, *Pseudomonas* exotoxin), or they may be synthetic or synthetic versions of naturally occurring toxins. In one particular example, the toxin is coupled to HLA-E by means of a linker molecule that introduces a disulphide bond between the HLA-E and the toxin (Vitetta et al, *Biol. Therapy of Cancer,* 1991, 482-495; Myers et al, *J. Immunol. Methods,* 1991, 131: 221-237). Thioether or other related compounds may be used to form non-reducible linkages. In another example, the toxin is expressed as a fusion protein with the HLA-E molecule, by splicing the gene encoding the toxin to the gene encoding the ligand to create a recombinant fusion protein (Pastan et al, *Annu. Rev. Biochem.,* 1992, 61: 331-354). Such fusion proteins may also include a biotinylation site to enable the creation of tetrameric or multimeric complexes of the toxin and HLA-E.

In general, the HLA-E described herein for use in detecting and separating and targeting toxins to CD94/NKG2+ cells will be a soluble HLA-E molecule. The term "soluble" is used herein in the manner in which it is conventionally used in the art in relation to cell surface receptors. A soluble form of a cell surface receptor is usually derived from the native form by deletion of the transmembrane domain. The protein may be truncated by removing both the cytoplasmic and the transmembrane domains, or there may be deletion of just the transmembrane domain with part or all of the cytoplasmic domain being retained. The important thing is that the desired extracellular function of the receptor is retained, which in this case is the CD94/NKG2-binding capability of the HLA-E binding domain. Wild type HLA-E may be modified to achieve the desired form by proteolytic cleavage, or by expressing a genetically engineered truncated or partially deleted form.

HLA-E for use in the invention which is present at surface of a cell on the other hand is preferably, although not necessarily, a membrane-bound form of HLA-E containing a transmembrane domain. It may or not also have a cytoplasmic domain. In order to get HLA-E expressed at the surface of a cell which does not normally express HLA-E at its surface, it is necessary to provide a peptide which binds in the HLA-E peptide binding groove. The peptide may be derived either from an HLA leader sequence which is permissive for HLA-E expression, or it may be derived from another source which expresses peptides that bind to HLA-E and induce its expression. Such other sources include viruses which escape NK cell-mediated cytotoxicity be encoding a peptide which binds to HLA-E and induces its expression. For example, the human cytomegalovirus (HCMV) encodes a protein known as UL40 (Accession No. p16780) which possess a peptide capable of binding to HLA-E (see fourth leader sequence peptide listed in Table 1).

Thus, HLA-E expression at the surface of a non-human mammalian cell may be achieved for example by co-transfecting the cell with nucleic acid encoding HLA-E and another HLA class I which has a leader sequence peptide capable of binding to HLA-E. Alternatively the cell may be co-transfected with nucleic acids encoding HLA-E and UL40 of HCMV. The inventors have shown that when transfected with UL40, cells expressing HLA-E intracellularly are induced to express HLA-E at the cell surface. Instead of co-transfecting the cells with two different sequences, the cells can be transfected with a single vector containing both sequences, or more conveniently, with a chimeric nucleic acid which encodes a fusion protein of HLA-E with the peptide. This chimeric nucleic acid may be for example a recombinant nucleic acid encoding HLA-E, in which the leader sequence of HLA-B8 replaces the leader sequence of HLA-E. In another example, the nucleic acid encodes HLA-E linked to the peptide via a linker of sufficient length to allow the peptide to locate in the peptide-binding groove while also remaining covalently attached to the HLA-E molecule. In this instance, the peptide is not a part of the leader sequence which is cleaved off, and is instead linked to the mature HLA-E molecule which is expressed at the cell surface. Advantageously, the peptide is linked to the HLA-E heavy chain via the HLA-E N-terminus (the α-1 domain). Such MHC-linked peptides are described in the published literature (see for example Mottez et al *J. Exp. Med.,* 1995, 181:493-502). It may also be advantageous to express the HLA-E heavy chain and β2m as a fusion protein. Such fusions are described in the literature (see for example Toshitani et al, *PNAS,* 1996, 93:236). Thus, the HLA-E-peptide molecule may be expressed from a single coding sequence.

For the provision of HLA-E at the cell surface in organs or tissues to be transplanted into another species, suitable transgenic animals can be produced. Techniques for generating transgenic animals such as transgenic pigs or rats or mice are well known in the art. For the purposes of the invention, nucleic acid material which expresses HLA-E and a suitable HLA-E binding peptide in the recipient organism is introduced into cells of the organism at the appropriate early stage of development. Individual animals which express HLA-E at the surface of their cells are then selected. Organs or tissues from those animals provide xenogeneic material for transplantation.

The absence of HLA-E in xenogeneic cells makes them susceptible to NK cell-mediated lysis because their MHC class I molecules fail to be recognised by human killer cell inhibitory receptors. This is evident from inducing expression of HLA-Cw0301 on porcine endothelial cells, which protects the porcine cells against xenogeneic cytotoxicity mediated by NK cells expressing the inhibitory NK receptors binding to HLA-Cw0301 (Seebach et al, *J. Immunol.,* 1997, 159:3655). There is evidence that NK cells play a role in the cellular immune response against xenografts (reviewed in Kaufman et al, *Ann. Rev. Immunol.,* 1995, 13:339 and Bach et al, *Immunol. Today,* 1996, 17:379). The endothelium is the first site of contact between a vascularized xenograft and the recipient immune system. It has been shown that human NK cells adhere to the vascular endothelium and infiltrate into the xenogeneic organs (Kirk et al, *Transplantation,* 1993, 56:785; Inverardi, *Immunol. Rev.,* 1994 141:71) and that NK cells directly activate porcine endothelial cells (Goodman et al, *Transplantation,* 1996, 61:763). It has been observed that xenogeneic human anti-porcine cytotoxicity in vitro includes an important MHC unrestricted contribution from polyclonal NK populations (Inverardi, *Immunol. Rev.,* 1994, 141:71; Kirk et al, *Transplantation,* 1993, 55:294; Seebach et al, *Xenotransplantation,* 1996, 3:188). It has also been shown that transgenic mice expressing a killer cell inhibitory receptor from the immunoglobulin superfamily, CD158, which recognises HLA-Cw3, are prevented from rejecting H-2 mismatch bone marrow grafts which express the cognate MHC class I HLA-Cw3 allele (Cambiaggi et al, *PNAS,* 1997, 94(15):8088-92. Thus, an HLA-E transgenic animal can be used to provide organs which will not be prone to attack by human NK cells expressing CD94/NKG2A receptors.

Xenogeneic transplantation will also involve the use of other mechanisms and/or reagents for the purpose of improving transplant survival. In particular, immunosuppressive agents may be employed. Immunosuppressive drugs are commonly used in transplantation therapy.

Currently, the primary animal species proposed as sources of xenografts are pigs and baboons (and possibly cows). Examples of particular treatments currently under consideration are:

treatment of Parkinson's disease by implantation of porcine foetal neuronal tissue;

treatment of diabetes mellitus by implantation or infusion of encapsulated porcine pancreatic islet cells;

treatment of hepatic failure by perfusion through or implantation of whole pigs livers;

(see Deacon, *Nat. Med.,* 1997, 3:350; Tibell, *Transplant. Proc.,* 1994, 26:762; Cramer, *Transplant. Proc.,* 1995, 27:80).

It will be evident that in addition to any special features such as the absence of transmembrane and/or cytoplasmic domains, or the presence of biotinylation sites required for multimerisation, the recombinant HLA-E used in the invention may have other features which make it different to native HLA-E. For example, the recombinant HLA-E may have deletions or insertions or altered residues compared to native HLA-E, which result in improved properties such as enhanced binding capability or improved stability, for use in accordance with the invention. HLA-E having improved stability at elevated temperatures, such as temperatures over 4° C. and/or over room temperature and/or at or around 37° C., will be of particular interest.

HLA-E in recombinant form as described herein is also provided in formulations suitable for in vivo use. Such formulations comprise a pharmaceutically acceptable diluent or carrier.

HLA-E itself exhibits very little polymorphism. The sequences for two different alleles of HLA-E can be found in the following data base locations: E*0101 at M20022 (arg in the residue at position 107); E*01031 at M32507 (glycine residue at position 107).

Some further, known techniques the principles of which may be additionally applied in the separation, identification or targeted killing methods of the invention are discussed below.

Some known separation methods will be adaptable for use in the separation or isolation of CD94/NKG2+ cells using HLA-E. For example, T cell populations can be isolated by use of antibody-coated plates. The antibodies are specific for particular cell-surface markers. Cell separation can be a negative selection process or a positive selection process (Wysocki et al, 1978 PNAS 75:2840-2848). HLA-E coated plates may be used to separate CD94/NKG2+ cells.

Immunomagnetic purification of a T cell subpopulation can also be realised using suitable antibodies coated on magnetic beads, in a negative or a positive selection process (Funderud et al 1987 in Lymphocytes: A Practical Approach Oxford University Press, New York 55-61). HLA-E-coated beads may be similarly employed for selection of CD94/NKG2+ NK cells and T cells.

FACS (fluorescence activated cell sorting) techniques may also be employed. Cell sorting of fluorescence-labelled cells uses flow cytometry to monitor the expression of specific intracellular and cell surface molecules and sort cell populations (Fleisher et al 1988 Cytometry 9:309-315).

Techniques which may be used in accordance with the invention for selective depletion or targeted killing of CD94/NKG2+ cells in a mixed cell population include antibody/complement-mediated cytotoxicity. Using a complement-fixing antibody, the cells expressing the marker recognised by the antibody can be lysed in presence of complement (Bianco et al 1970 J. Exp. Med. 132:702-720). For example, an anti-HLA-E antibody may be employed to selectively destroy cells to which HLA-E is bound.

TABLE I

Examples of peptides generated from MHC class I leader sequences at residues 3-11

| Leader sequence peptide (3-11) from MHC class I | Binding to HLA-E in vitro |
|---|---|
| VMAPRTLVL | + |
| VMAPRTLLL | + |
| VMAPRTVLL | + |
| VMAPRTLIL | + |
| VMAPRTLFL | + |
| VMGPRTLVL | +/− |
| VTAPRTVLL | − |
| VTAPRTLLL | − |
| VMPPRTLLL | + |
| VMEPRTLIL | − |
| VMAPRALLL | − |

EXAMPLES

Example 1

Construction of HLA-E Tetrameric Complexes

HLA-E tetrameric complexes were constructed by refolding recombinant HLA-E and β2m molecules in vitro with a synthetic peptide (VMAPRTVLL) [SEQ ID NO 3] derived from residues 3-11 of the signal sequence of HLA-B*0801. A biotinylation site was engineered in the C terminus of the HLA-E heavy chain, allowing HLA-E/β2m/peptide complexes to be enzymatically biotinylated using E. coli BirA enzyme and conjugated with phycoerthrin (PE)-labeled Extravidin to create tetrameric complexes. HLA-A and -B tetramic complexes have proved to be very efficient at specifically binding to T cell receptors on antigen-specific CD8* T cells from peripheral blood in vitro (Altman et al 1996 Science 274: 94-96).

Methods

HLA-E was cloned by RT-PCR with primers COO7 and COO6 from RNA extracted from monocytes of an HLA-E*0101 homozygous individual. The N terminal nucleotide sequence was synonymously altered by PCR mutagenesis using the primers CO17 and COO6 to optimise protein expression from the pGMT7 vector in E. coli. The coding sequence for the extracellular portion of HLA-E (residues 1-276) was amplified using the primers CO17 and CO23 and recloned into a pGMT7 derivative to produce the expression plasmid COCO92 which contains the BirA recognition and biotinylation site in frame at the 3' end of the HLA-E heavy chain. Primers were:

COO6 gtgggctaagcttacggcttccatctcagggtgacgggctc [SEQ ID NO: 12]

COO7 ctacgggcatatggtagatggaaccctccttttactctcc [SEQ ID NO: 13]

CO17 ccgtacctcgagcatatgggttctcat-tctttaaaatattttcatacttctgtatctagacccggccg [SEQ ID NO: 14]

O23 tggtgtctagaggatcctggcttccatctcagggtgacgggctcg [SEQ ID NO: 15]

HLA-E tetrameric complexes were generated essentially as described (Altman et al 1996). Briefly, HLA-E and β2m proteins were over-expressed in E. coli strains BL21 (DE3) pLysS and XA90 respectively, purified from inclusion bodies, solubilised into a urea solution, then refolded by dilution in vitro with a synthetic peptide (VMAPRTVLL) [SEQ ID NO 3] from HLA-B*0801 leader sequence (Research Genetics). HLA-E heavy chain/β2m/peptide complexes were biotinylated with BirA enzyme, purified by FPLC and Mono-Q ion exchange chromatography, then complexed in a 4:1 molar ratio with Extravidin-PE (Sigma).

Example 2

Binding of HLA-E Tetramers

Peripheral blood mononuclear cells (PBMC) from 9 normal donors were stained with HLA-E tetramer prepared as described in Example 1 and compared to staining observed with an HLA-A2 tetramer refolded with Epstein Barr Virus (EBV) lytic cycle BMLF1 259-267 peptide epitope (Steven et al 1997 J. Exp. Med. 185: 1605-17). A high frequency of lymphoid cells were stained with the HLA-E tetramer (range 2 to 11%) (FIG. 1A), whereas the HLA-A2 tetramer generally stained 0 to 0.8% of the lymphocytes in EBV-seropositive donors (FIG. 1C). By setting an electronic gate on the lymphocytes binding HLA-E tetramer, we observed that a large proportion were NK cells (typically 40 to 80% CD3$^-$, CD56$^+$) but a significant subset were T cells (typically 15 to 50% CD3$^+$), some of which were also expressing CD56 (FIG. 1B). About 2% of the lymphocytes binding HLA-E tetramer were CD4+ T cells, and about 5% were CD19$^+$ B cells, but these could represent non-specific binding because of similar staining with the HLA-A2 tetramer (data not shown). The HLA-A2 tetramer did not bind to CD56$^+$ cells but, in EBV-seropositive donors, bound to EBV specific CD3$^+$, CD8$^+$ T cells (FIG. 1D), confirming previous studies on the specificity of MHC-tetrameric complexes for T cells bearing a specific T cell receptor (Altman et al 1996).

HLA-E tetramer staining was abolished when the PBMC and the tetramer were incubated in the presence of the antibody HP3D9 (Aramburu et al 1990 Immunol. 144: 3238-47) against CD94, an NK cell receptor belonging to the C-type lectin superfamily (Chang et al 1995 Eur. J. Immunol. 25: 2433-37) (FIG. 2A). As the antibody HP3D9 was diluted, the HLA-E tetramer staining was restored (data not shown). The interaction between HLA-E and CD94 was also confirmed by staining a number of well-characterised $CD94^+$ NK clones with HLA-E tetramer and demonstrating that another anti-CD94 mAb (DX22) (Phillips et al 1996 *Immunity* 5: 163-172) completely inhibited HLA-E tetramer binding (FIG. 2B, and data not shown). No staining with HLA-A2 tetramer was found on $CD94^+$ NK clones (data not shown).

To characterise further the NK receptor interacting with HLA-E, we stained P815 and 293T cells transfected with these receptors. No HLA-E tetramer staining was observed on P815 stably transfected with CD94 alone or NKG2B alone (FIG. 3A), nor on 293T transiently transfected with CD94 or NKG2A alone (data not shown). In contrast, HLA-E tetramer bound to 293T cells cotransfected with CD94 and NKG2A, CD94 and NKG2B, or CD94 and NKG2C (FIG. 3B). Expression of the heterodimers on these transfectants was monitored using a polyclonal rabbit serum that reacts with CD94/NKG2A, NKG2B and NKG2C heterodimers (Lazetic et al 1996 *J. Immunol.* 157: 474145). This result was confirmed using mouse pre-B Ba/F3 cells stably transfected with CD94/NKG2C or NK clones expressing the inhibitory receptor CD94/NKG2A (FIG. 2B and data not shown). Carbohydrates on HLA-E are not necessary for binding, as the recombinant HLA-E used to make the tetramer was produced in *E. coli. This is quite surprising given that both CD*94 and NKG2 proteins are members of the C-type lectin superfamily. Carbohydrate residues may form additional points of interaction increasing the affinity of binding.

We have also shown that HLA-E does not interact with other killer cell inhibitory cell receptors (KIR) as no staining with the HLA-E tetramer was observed on Ba/F3 cells transfected with KIR2DL1 (NKAT1 or p58), KIR2DL3 (NKAT2 or p58), KIR3DL1(NKAT3 or p70), KIR3DL2 (NKAT4 or p70/140), KIR2DS2 (NKAT5 or p50), KIR2DL2 (NKAT6 or p58) or KIR2DS4 (NKAT8 or p50) (Lanier et al 1997 *Immunol. Rev.* 155: 145-154). Furthermore, staining of PBMC with HLA-E tetramer was not blocked by antibodies against any of these KIR receptors: EB6 (anti-KIR2DL1), GL183 (anti-KIR2DL3, -KIR2DS2, -KIR2DL2), DX9 (anti-KIR3DL1), or 5.133 (anti-KIR3DL1, -KIR3DL2) (data not shown). Thus, the CD94/NKG2 receptors appear to be unique and specific receptors for HLA-E recognition.

We have previously reported that HLA-E, like the mouse Qa-1 molecule (Aldrich et al 1994 *Cell* 79: 649-658; DeCloux et al 1997 *J. Immunol.* 158: 2183-2191; Cotterill et al 1997 *Eur. J. Immunol.* 27: 2123-2132) can bind signal sequence-derived peptides from MHC class I molecules in vitro (Braud et al 1997) and recently showed that HLA-E cell surface expression is regulated by the binding of such peptides (Braud et al 1998). Most HLA-A and HLA-C alleles possess a leader peptide 3-11 that binds to HLA-E whereas only a third of HLA-B alleles do. The remaining B alleles have a Threonine at position 2 in the peptide instead of a Methionine. This substitution at a primary anchor residue disrupted peptide binding to HLA-E as measured in an in vitro peptide binding assay previously described (Braud et al 1997) (Table 2). Transfection of MHC class I alleles which have a leader peptide capable of binding to HLA-E into HLA-A, -B, -C, -G negative 721.221 cells resulted in expression of the endogenous HLA-E on the cell surface of 721.221 cells. When the leader sequence peptide was not capable of binding, no such upregulation of HLA-E at the cell surface was observed.

It has been shown previously that NK cells expressing an inhibitory CD94/NKG2A receptor do not kill 721.221 cells transfected with certain HLA-A, -B, -C, or -G alleles, but are able to lyse these transfectants in the presence of neutralizing anti-CD94 or anti class I antibodies (Phillips et al 1996 *Immunity* 5: 163-172; Sivori et al 1996 *Eur. J. Immunol.* 26:2487-2492; Sivori et al 1996 *Transplant* 28: 3199-3203). A striking correlation between the presence of an HLA class I leader sequence peptide capable of binding to HLA-E causing its surface expression and the specificity of the CD94/NKG2A inhibitory receptor is shown in Table 2. All the MHC class I alleles which, upon transfection, protect 721.221 cells to from killing by CD94/NKG2A+ NK clones have a peptide capable of binding to HLA-E. Similarly, all HLA alleles incapable of protecting against these clones lack an HLA-E binding leader peptide. Together with the direct evidence for physical interaction between HLA-E and CD94/NKG2A, these results indicate that inhibition by the CD94/NKG2A receptor is mediated by recognition of HLA-E rather than a broad range of HLA-A, -B, and -C molecules. In further support of this, the HLA-A2 tetramer refolded around a Tax peptide epitope of human T-cell lymphotropic virus HTLV1 (Garboczi et al 1996 *Nature* 384: 134-141) did not bind to CD94/NKG2A transfectants or NK cells expressing CD94/NKG2 receptors, despite the fact that HLA-A2 has been shown to have a protective effect against CD94/NKG2A+ NK clones and HLA-A2 target cell protection can be reversed in the presence of anti-CD94 or anti-class I antibodies. Furthermore we confirmed, by immunoprecipitation that the anti-class I antibody DX17, which inhibits interactions between class I molecules and CD94/NKG2A, also recognises HLA-E.

It has recently been demonstrated that recognition of 721.221 target cells by $CD94/NKG2^+$ NK clones can be inhibited by transfection of HLA-G, another nonclassical class I molecule mainly expressed on trophoblast cells (Soderstrom et al 1997 *J. Immunol.* 159: 1072-1075; Perez Villar et al 1997 *J. Immunol.* 158: 5736-5743; Pende et al 1997 *Eur. J. Immunol.* 27: 1875-1880). However, HLA-G also possesses a leader sequence peptide capable of binding to HLA-E and 721.221-G transfectants express a significant level of HLA-E. Similarly, Reyburn et al 1997 (*Nature* 386: 514-517) recently reported that human cytomegalovirus encodes a viral protein (UL18), with similarity to MHC class I, that can protect 721.221 cells from NK cell lysis, possibly involving CD94 receptors. Whether these observations can be explained by binding of HLA-G or UL18 leader peptides to the endogenous HLA-E molecules in 721.221 is under investigation.

HLA-E also binds to CD94/NKG2C which has been shown to activate cytolytic activity in NK cell transfectants (Houchins et al 1997 *J. Immunol.* 158: 3603-3609) indicating that HLA-E is involved in regulating NK cell-mediated cytotoxicity via both CD94/NKG2A and CD94/NKG2B is inhibitory NK cell receptors and CD94/NKG2C stimulatory NK cell receptors. Our present results demonstrate a novel role for a non-classical class I molecule HLA-E and identify its predominant receptor. It remains to be determined whether the strong preference of HLA-E for binding signal sequence-derived peptides is simply to permit expression of HLA-E or whether it is implicit in recognition by CD94/NKG2 receptors.

TABLE 2

| .221 cells tranfected with HLA class I alleles | Inhibition of killing by CD94/NKG2A + NK clones* | Presence of leader sequence peptide capable of binding to HLA-E§ | HLA leader sequence peptide (residues 3-11) | Concentration of peptide required to obtain 50% of binding to HLA-E† |
|---|---|---|---|---|
| .221 | – | –‡ | | |
| .221-A*0201 | + | + | VMAPRTLVL | 0.06 μM |
| .221-A*0211 | + | + | VMAPRTLVL | 0.06 μM |
| .221-A*2501 | + | + | VMAPRTLVL | 0.06 μM |
| .221-A*2403 | + | + | VMAPRTLVL | 0.06 μM |
| .221-A*3601 | + | + | VMAPRTLLL | 0.3 μM |
| .221-B*0702 | + | + | VMAPRTVLL | 0.06 μM |
| .221-Cw*0102 | + | + | VMAPRTLIL | 0.3 μM |
| .221-Cw*0401 | + | + | VMAPRTLIL | 0.3 μM |
| .221-Cw*0304 | + | + | VMAPRTLIL | 0.3 μM |
| .221-Cw*0801 | + | + | VMAPRTLIL | 0.3 μM |
| .221-G | + | + | VMAPRTLFL | 0.3 μM |
| .221-B*1501 | – | – | VTAPRTVLL | >100 μM |
| .221-B*5101 | – | – | VTAPRTVLL | >100 μM |
| .221-B*5801 | – | – | VTAPRTVLL | >100 μM |
| .221-B*4601 | – | – | VTAPRTVLL | >100 μM |
| .221-B*5401 | – | – | VTAPRTLLL | >100 μM |
| .221-B*5501 | – | – | VTAPRTLLL | >100 μM |

SEQ ID NOS: 1, 1, 1, 1, 2, 3, 4, 4, 4, 4, 5, 7, 7, 7, 7, 8, 8, respectively.
*Results published by Phillips et al 1996
†A peptide binding assay was developed in vitro. Results are expressed as a ratio of optical densities referred to as percentage of binding to HLA-E (Braud et al 1997)
‡The HLA-A, -B, -C, and -G negative .221 cells express HLA-E and HLA-F which have a shorter leader sequence and lack the appropriate peptide capable of binding to HLA-E.
§The presence of a leader sequence peptide capable of binding to HLA-E upregulates HLA-E surface expression as measured on .221 and .221 cells transfected with HLA-A or –B alleles using the antibody DT9 recognizing HLA-E and HLA-C alleles Figure Legends for Example 2

FIG. 1 HLA-E Tetramer Binds NK Cells and a Subset of T Cells

Flow cytometry analysis on gated peripheral blood lymphocytes from normal EBV seropositive donor VB using (A) HLA-E tetramer refolded around the leader sequence peptide residues 3-11 from HLA-B*0801 or (C) HLA-A2 tetramer refolded around the Epstein Barr Virus (EBV) lytic cycle BMLF1 259-267 peptide epitope (Steven et al 1997). The phenotypes of (B) HLA-E tetramer or (D) HLA-A2 tetramer binding lymphocytes were further investigated in triple colour stains as indicated. Percentages in each quadrant are represented by the cross in the upper right. Within the total CD3–, CD56+ NK cell population, 10.3% of cells bound HLA-E tetramer, and within the total CD3+ T cell population, 2.2% of cells bound HLA-E tetramer. In contrast, less than 0.2% of CD3–, CD56+ cells bound HLA-A2 tetramer, whereas 1% of CD3+ T cells bound HLA-A2 tetramer.

Figure 2:
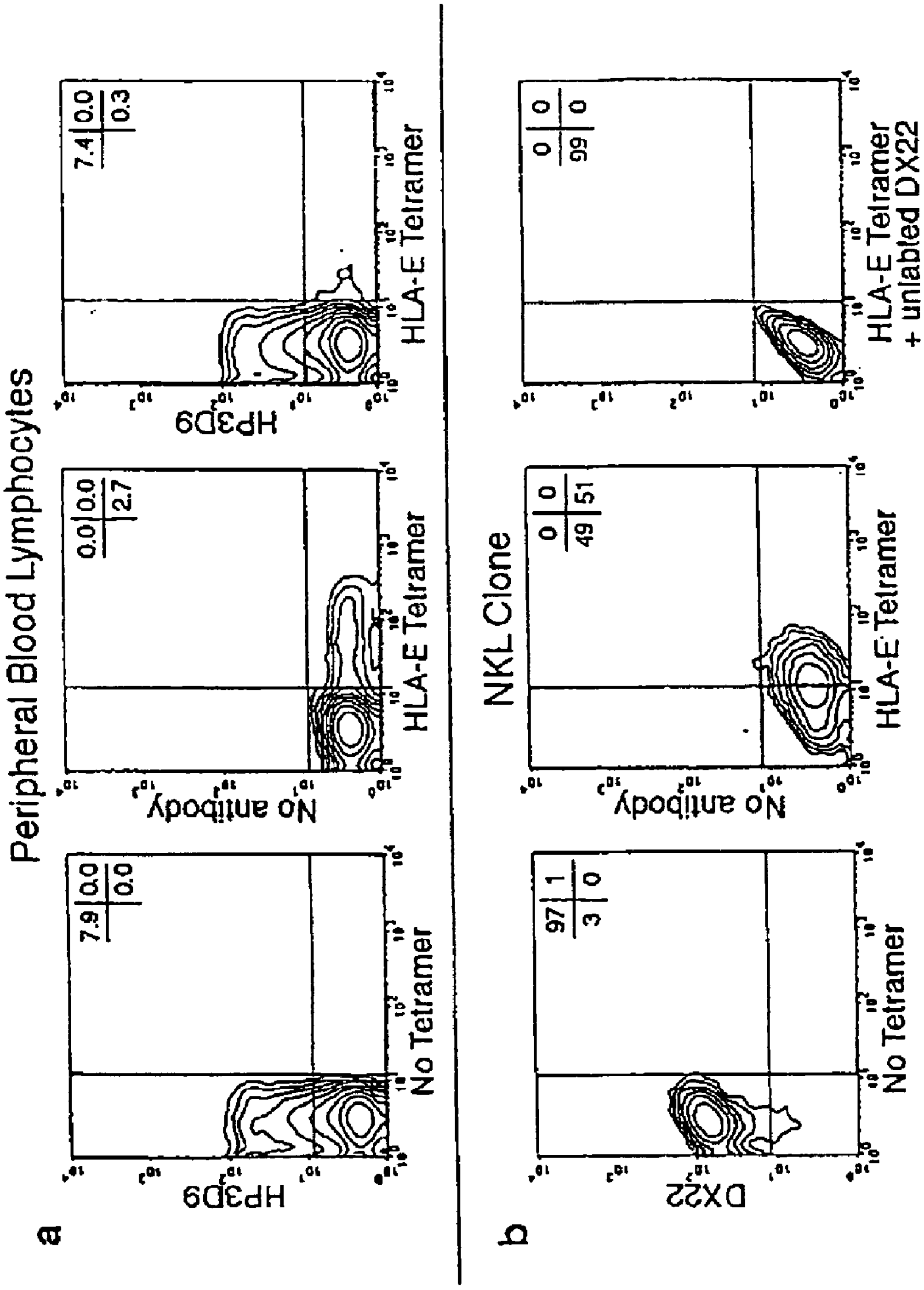
FIG. 2 illustrates a series of graphs showing HLA-E tetramer staining is inhibited by anti-CD94 antibodies.

FIG. 2 HLA-E Tetramer Staining is Inhibited by Anti-CD94 Antibodies (A) Peripheral blood lymphocytes from normal donor SRJ were stained with the anti-CD94 antibody HP3D9 (Aramburu et al 1990) (1/50 dilution of ascites) followed by FITC-anti-mouse IgG $(Fab')_2$ (Sigma); HLA-E tetramer-PE alone; or HLA-E tetramer-PE in the presence of HP3D9 (1/50) which inhibited HLA-E tetramer staining.

(B) The NK cell line NKL (Robertson et al 1996 *Exp. Haematol.* 24: 406-415) expressing the NK receptor CD94/NKG2A but none of the KIR molecules was stained with the anti-CD94 antibody DX22 (Phillips et al 1996) (1 mg) followed by PE-anti-mouse IgG; HLA-E tetramer-PE; or HLA-E tetramer-PE in the presence of 1 mg of DX22 antibody which inhibited HLA-E tetramer staining. Percentages in each quadrant are listed in the upper right. The HLA-A2 tetramer refolded around the HTLV1 Tax peptide (Garbocz et al 1996) did not bind to NKL (data not shown).

Figure 3:
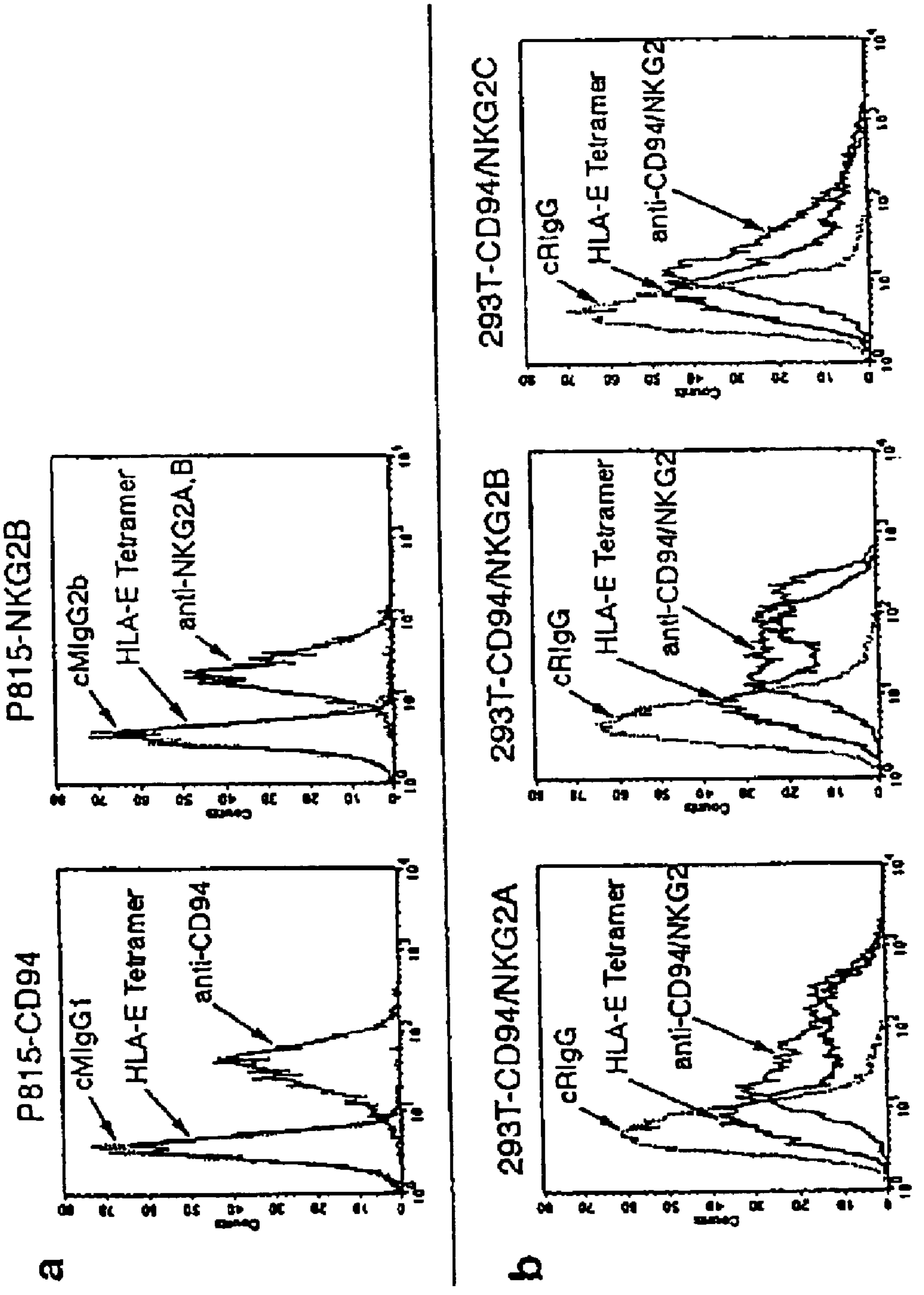
FIG. 3 illustrates a series of graphs showing HLA-E binds to NK cell CD94/NKG2A, CD94/NKG2B and CD94/NKG2C receptors but not to CD94 or NKG2 alone.

FIG. 3 HLA-E Binds to NK Cell CD94/NKG2A, CD94/NKG2B and CD94/NKG2C Receptors but not to CD94 or NKG2 Alone.

(A) P815 cells were stably transfected with pBJ-neo vector containing human CD94 cDNA (Chang et al 1995) or NKG2B cDNA (Houchins et al 1991 *J. Exp. Med.* 173:1017-20). Cells were stained with PE-control mouse IgG1 (cMIgG1) or IgG2b (cMIgG2b), anti-CD94 antibody DX22-PE, anti-NKG2A and B antibody DX20-PE, or HLA-E tetramer-PE. Neither P815 transfectant stained with HLA-E tetramer or HLA-A2 HTLV1 Tax peptide tetramer. (B) 293T cells stably transfected with CD94 were transiently transfected with NKG2A, NKG2B, and NKG2C (Lazetic et al 1996). Flow cytometry staining was performed using rabbit preimmune serum (cRIgG) 1/500 final dilution or rabbit anti-CD94/NKG2 heterodimer serum (anti-CD94/NKG2) 1/500 final dilution, both followed by FITC-anti-rabbit IgG, or with HLA-E tetramer-PE. No staining with HLA-A2-HTLV1 tax peptide tetramer was observed. Staining of 293T-CD94 cells cotransfected with a control plasmid were not stained by HLA-E tetramer or the rabbit anti-CD94/NKG2 serum (data not shown).

Example 3

Transfection of Cells with HLA-E-Binding Leader Sequences to Enable HLA-E Expression and Protection Against NK Cell Clones Methods Human NK-cell clones were established and cultured as described (Litwin et al 1993 *J. Exp. Med.* 178: 1321-1336). Cytotoxicity assays were performed as described (Phillips et al 1996 *Immunity* 5:163-172). A chimeric cDNA containing the leader segment of HLA-G and the extracellular, transmembrane, and cytoplasmic domains of HLA-B*5801 was generated by PCR using the following oligonucleotide primers: sense primer 1,5'-GCGTCTAGAATGGTGGTCATGGCACCCCGA-3'[SEQ ID NO: 16]; antisense primer 1,5'-CATGGAGTGGGAGCCGGCCCAGGTCTCGGT-3'[SEQ ID NO: 17]; sense primer 2,5'-GGCTCCCACTCCATGAGGTAT-3'[SEQ ID NO: 18]; and antisense primer 2,5'-GCTGTGAGAGACA-3'[SEQ ID NO: 19].

PCR was performed using a wild-type HLA-G cDNA as a template with primer set 1 and using wild-type HLA-B*5801 cDNA as a template with primer set 2. Products from these PCR reactions were mixed and used as templates for a subsequent reaction with sense primer 1 and antisense primer 2. The product was digested with XbaI and HindIII and ligated into the pBJneo vector.

A chimeric cDNA containing the leader segment of HLA-B*0702 and the extracellular, transmembrane and cytoplasmic domains of mouse CD80 (or B7-1) was generated by PCR using the following oligonucleotide primers: sense primer 3,5'-ACCGAGACCTGGGCCGTTGATGAACAAACTG-3'[SEQ ID NO: 20]; antisense primer 3,5'-GCAAGCTTCTAAAGGAAGACGGTCTGTTC-3' [SEQ ID NO: 21]; sense primer 4,5'-GGGCGTCGACCCGGACTCAGAATCTCCTCAGACGCCGAG-3' [SEQ ID NO: 21]; and antisense primer 4,5'-CAGTTGTTCATCAACGGCCCAGGTCTCGGT-3' [SEQ ID NO: 23].

PCR was performed using a wild-type mouse CD80 cDNA as a template with primer set 3 and using wild-type HLA-B*0702 cDNA as a template with primer set 4. Products from these PCR reactions were mixed and used as templates for a subsequent reaction with sense primer 4 and antisense primer 3. The product was digested with SalI and HindIII and ligated into the pBJneo vector. PCR products were verified by sequencing. 721.221 B-lymphoblastoid cells were transfected with the wild-type and chimeric cDNAs and selected as described (Litwin et al 1993).

Results

To determine whether the presence of an HLA-E binding leader peptide that induces surface expression of HLA-E is enough to provide protection against CD94/NKG2A$^+$ NK-cell clones, a chimeric complementary DNA (GLS-B*5801) was generated. It contained the leader segment of HLA-G (from which a peptide can bind to HLA-E; Table 2) and the extracellular, transmembrane and cytoplasmic domains of HLA-B*5801 (an HLA molecule that is not implicated in recognition by CD94/NKG2A receptors—Phillips et al 1996 *Immunity* 5: 163-172). Stable 721.221 cell line transfectants were selected and analysed for susceptibility to lysis by NK-cell clones expressing CD94/NKG2A receptors. As shown in FIG. 4*a*, an NK-cell clone expressing a CD94/NKG2A receptor efficiently killed untransfected 721.221 cells as well as 721.221 cells transfected with wild-type HLA-B*5801. However, protection against NK-cell-mediated lysis was conferred by expression of the chimeric GLS-B*5801 molecule but reversed in the presence of antibodies against either CD94 or HLA class I molecules. A chimeric cDNA (B7LS-mCD80) containing the leader segment of HLA-B*0702 (with a peptide that can bind to HLA-E; Table 2) and the extracellular, transmembrane and cytoplasmic domains of mouse CD80 was transfected into 721.221 cells and tested for lysis by CD94/NKG2A$^+$ NK-cell clones. CD80 is an adhesion cell surface molecule expressed on activated B and T cells and macrophages. In this experiment CD80 is used as an irrelevant control molecule to show that only the leader sequence of MHC class I molecules is necessary to upregulate HLA-E and induce a protective effect. There was less lysis of 721.221 cells expressing the B7LS-mCD80 molecule but not of cells expressing wild-type CD80, and protection was reversed by anti-CD94 but not control antibodies (FIG. 4*b*). These results indicate that an HLA-E binding leader peptide alone is enough to protect 721.221 cells from lysis by NK-cell clones expressing inhibitory CD94/NKG2A-type receptors.

These results provide further confirmation of HLA-E as a ligand for CD94/NKG2A.

Figure Legends for Example 3

Figure 4:
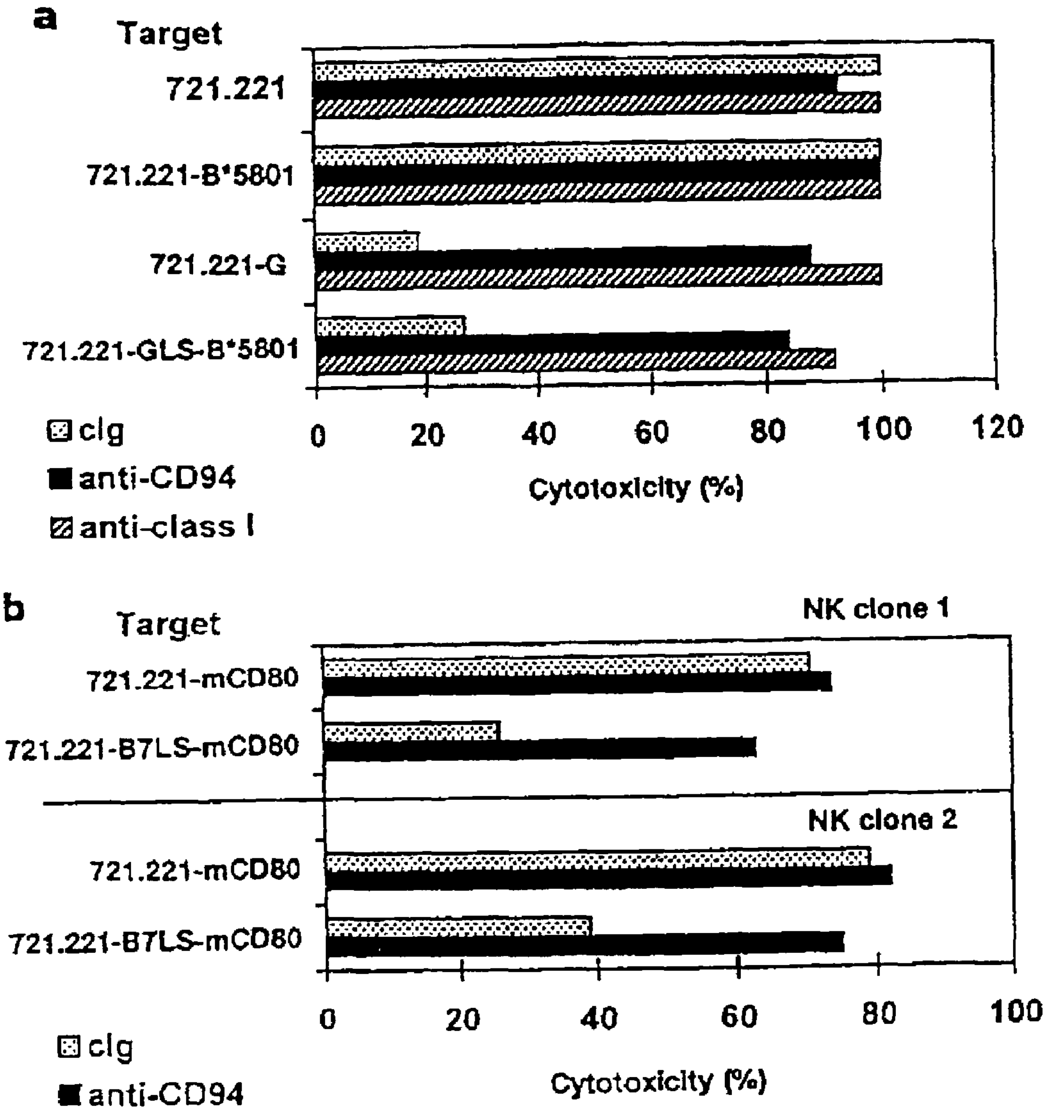
FIG. 4 illustrates a series of graphs showing HLA-E mediates inhibition of NK cells through interaction with CD94/NKG2A.

FIG. 4 HLA-E Mediates Inhibition of NK Cells Through Interaction with CD94/NKG2A.

(A) Lysis of 721.221 cells expressing HLA-B*5801, HLA-G or a chimeric is molecule (GLS-B*5801) containing the HLA-G leader sequence and the extracellular, transmembrane, and cytoplasmic domains of HLA-B*5801 by a representative NK-cell clone expressing the CD94/NKG2A receptor. Assays were performed at an effector to target ratio of 0.5:1, in the presence of control immunoglobulin (clg), anti-CD94 (DX22), or anti-HLA class I (DX17) at 5 μg $ml^{-1}$. (B) Lysis of 721.221 cells expressing mouse CD80 or a chimeric molecule (B7LS-mCD80) containing the HLA-B*0702 leader sequence and the extracellular, transmembrane, and cytoplasmic domains of mouse CD80 by two representative NK-cell clones expressing the CD94/NKG2A receptor. Assays were performed at an effector-to-target ratio of 1:1 in the presence of control immunoglobulin (clg) or anti-CD94 (DX22) at 10 μg $ml^{-1}$.

Example 4

Isolation of CD94/NKG2+ cells by Fluorescence Activated Cell Sorting

Peripheral blood mononuclear cells (PBMC) were obtained from venous blood which had been taken from donors into tubes containing Heparin. Briefly, blood samples were diluted 1:1 with serum free RPMI-1640 and 10 ml of diluted blood was laid onto a 5 ml Ficoll-Hypaque gradient. After a centrifugation at 1200 rpm for 30 minutes, the PBMC at the interface were carefully removed and washed twice in RPMI. The first centrifugation was performed for 10 minutes at 2000 rpm and the second for 10 minutes at 1200 rpm to remove most platelets. PBMC were then diluted in RPMI and kept in sterile medium while processed.

Binding of HLA-E tetramer was monitored by flow cytometry and cells were sorted. PBMC ($5\times10^6$) were incubated for 15 minutes at 37° C. followed by 15 minutes at 4° C. with 12 μl of HLA-E tetramer labelled with phycoerythrin (PE). CD3 monoclonal antibody labelled with FITC was then added for another 15 minutes at 4° C. Cells were then washed twice and sorted on a FACScan, which measures fluorescent light emission and separates distinct cell populations by electrostatic-deflection (electronic cell sorting). Single cells or subsets of cells stained by HLA-E tetramer were collected in sterile 96 well plates and put in culture. NK cells (CD3−, HLA-E tet+) and T cells (CD3+, HLA-E tet+) were grown in Yssel's medium (Yssel et al, 1984, *J. Immunol. Methods,* 72:2199) in the presence of irradiated feeder cells (PBMC and JY BCL), 0.1 μg/ml of PHA, and 100 U/ml or 10 U/ml of IL-2 respectively. Autologous cells processed in this way are suitable for reinjection into patients. FACS techniques can also be used to count cells for quantitation purposes.

Suitable methods for culturing NK cells and clones are described in Litwin et al, *J. Exp. Med,* 1993, 178:1321-1336. Methods for maintaining T cells are described in Dunbar et al, *Current Biol.,* 1998, 8(7) 413 and Nixon et al, *Nature,* 1988. 336: 484-487.

Example 5

Isolation of CD94/NKG2+ Cells Using HLA-E-Coated Beads

Cells expressing CD94/NKG2 receptors were isolated with HLA-E-streptavidin coated dynabeads. Dynabeads M-280 Streptavidin are magnetic beads coated with streptavidin. Soluble HLA-E was engineered with a biotinylation site for BirA enzyme at the C terminus of HLA-E heavy chain and refolded with β2 microglobulin and a synthetic peptide derived from residues 3-11 of the signal sequence of some HLA molecules (described in Braud et al, 1998, *Nature,* 391:795). These HLA-E monomers were biotinylated using BirA enzyme and conjugated to Dynabeads M-280 using a standard protocol. Biotinylated HLA-E were incubated with PBS-washed Dynabeads M280 for 30 minutes at 4° C. with bidirectional mixing (2 μg HLA-E/$10^7$ Dynabeads). The beads were collected by placing the tube in a Dynal Magnetic Particle Concentrator (MPC) and the supernatant was removed. The beads were washed 5 times in the same way. HLA-E coated M-280 dynabeads were then mixed with isolated PBMC (obtained as described in Example 3) ($10^7$ beads/ml) and incubated for 20 minutes at 4° C. with gentle rotation. The tube was placed in a Dynal MPC and left to rest for 2 minutes. The supernatant was removed and the cells attached to the beads washed 5 times. Cells were then grown as described in Example 3.

NB: To deplete PBMC of cells expressing receptors for HLA-E, the supernatant is kept and the beads discarded.

Example 6

Targeted Killing of NK Cells

Recombinant biotinylated HLA-E is prepared as described in Example 1. A mixture containing biotinylated HLA-E and a biotinylated toxic agent such as the enzyme perforin in a molecular ratio of 3:1 is combined with extravidin to produce multimeric HLA-E linked to the toxic agent. A PBMC sample from a human donor is prepared according to standard techniques and contacted with the HLA-E reagent, resulting in killing of the CD94/NKG2+ cells present in the sample. CD94/NKG2 negative cells are recovered.

Example 7

Xenotransplantation

A recombinant DNA expressing HLA-E in which the leader sequence of HLA-E was replaced by the leader sequence of HLA-B8 was generated. This chimeric cDNA contains the leader sequence of HLA-B, and the extracellular (α1, α2 and α3), the transmembrane and the cytoplasmic domains of HLA-E. It was generated using the following oligonucleotide primers:

sense primer A:

5'-CTCGGCGGCCCTGGCCCTGACCGAGAC-CTGGGCGGGCTCCCACTCC TTG-3'[SEQ ID NO: 24]

antisense primer B:

5'-TTCTGTCTAGATTACAAGCTGTGAGACT-CAGACCCCTG-3'[SEQ ID NO: 25]

sense primer C:

5'-CTGACCGAATTCGCCGCCACCATGCTG-GTCATGGCGCCCCGAACCGT CCTCCTGCT-GCTCTCGGCGGCCCTGGCC-3'[SEQ ID NO: 26]

The PCR was performed using the cDNA of HLA-E as a template with primers A and B. The product from that PCR was then used as a template for a subsequent reaction with primers B and C. The last product was digested with EcoR1 and XbaI and ligated into the expression vector pcDNA3.

Transgenic animals are then produced as follows. Females are superovulated, mated to fertile males and sacrificed the following day. Zygotes with two pronuclei are recovered and one of the pronuclei is microinjected with the DNA expressing the HLA-E-HLA-B leader sequence construct. Surviving embryos are reimplanted into pseudopregnant foster females and DNA samples from new borns are evaluated for the presence of the foreign gene (HLA-E construct). These techniques are described in detail in the literature (eg Guide to techniques in mouse development, P. Wassarman and M DePamphilis, Methods in Enzymology (Academic Press), Section X: Transgenic animals: pronuclear injection (p 747-802) and Section XI: Transgenic animals: embryonic stem cells and gene targeting (p 803-932)).

Example 8

Stable Transfection of CD94 and NKG2 Genes into Mammalian Cells

Mouse cells (P815, L cells) were sequentially transfected by electroporation or calcium phosphate DNA precipitation respectively, with a mammalian expression vector pcDNA3 (neomycin resistance gene) containing CD94 cDNA and either NKG2A or NKG2C with DAP12. NKG2A and NKG2C cDNA was cloned into the expression vector pcDNA3.1/hygro vector (containing the hygromycin resistance gene) and DAP12 was cloned into the expression vector pcDNA3.1/zeo (zeomycin resistance). P815 cells were electroporated with 500 μF, 0.25 volt, and selection (G418 and hygromycin and zeomycin) was added 2 days later. Cells expressing a high level of receptors were sorted by flow cytometry. L cells were transfected by calcium phosphate DNA precipitation and selected in the presence of G418, hygromycin and zeomycin. Transfectants were cloned by limiting dilution and cell surface expression of the CD94/NKG2 receptors was monitored using specific antibodies.

The stable transfectants are useful for the identification of antibodies or other agents that interfere with HLA-E binding to CD94/NKG2. Agents which specifically interfere with HLA-E binding to either inhibitory CD94/NKG2 receptors (e.g. CD94/NKG2A) or stimulatory CD94/NKG2 receptors (e.g. CD94/NKG2C) can be identified by performing binding assays using two different transfectants. A list of known antibodies which interfere with HLA-E binding to CD94/NKG2 is given below:

Antibodies which block the interaction between HLA-E and CD94/NKG2 receptors:

1-Anti-HLA-E:—3D12 (Lee et al, 1998, *J. Immunol.* 160: 4951

2-Anti-CD94:

HP3D9 (Perez-Villar et al, 1995, *J. Immunol.* 154: 5779) commercialized by Pharmingen —HP-3B1 (Aramburu et al, 1990, *J. Immunol.* 144: 3238) commercialized by Immunotech —X1A85 (Sivori et al, 1996, *Eur. J. Immunol.* 26: 2487)

DX22 (Phillips et al, 1996, *Immunity,* 5:163) DNAX

3. Anti-NKG2A:

—Z199 (Carreto et al, 1997, *Eur. J. Immunol.* 27:563) commercialised by Immunotech —Z270 (Sivori et al, 1996, *Eur. J. Immunol.* 26: 2487)

The techniques described in this example may also be used to transfect mammalian cells such as murine L cells with nucleic acids encoding HLA-E as described herein.

The invention claimed is:

1. A method of testing a compound for biological activity, which method comprises:

(i) providing cells expressing a CD94/NKG2 receptor, wherein the NKG2 member is selected from the group consisting of NKG2A, NKG2B, NKG2C, NKG2E, and NKG2F at the cell surface;

(ii) contacting the cells with HLA-E in the presence of the test compound; and (iii) determining whether the presence of the compound affects the binding of HLA-E to the cells.

2. The method according to claim 1, wherein the CD94/NKG2 receptor is an inhibitory NK cell receptor.

3. The method according to claim 1, wherein the CD94/NKG2 receptor is a stimulatory NK cell receptor.

4. The method according to claim 1, wherein the NKG2 member is NKG2A.

5. The method according to claim 1, wherein the NKG2 member is NKG2C.

6. The method according to claim 1, wherein the NKG2 member is NKG2B.

7. The method according to claim 1, wherein the NKG2 member is NKG2E.

8. The method according to claim 1, wherein the NKG2 member is NKG2F.

9. The method of claim 1, wherein the test compound is an antibody.

10. A method of identifying a compound affecting the binding of HLA-E to CD94/NKG2 receptors, which method comprises:

(i) providing cells expressing a CD94/NKG2 receptor at the cell surface, wherein the NKG2 member is selected from a group consisting of NKG2A, NKG2B, NKG2C, NKG2E, and NKG2F;

(ii) contacting the cells with HLA-E in the presence of a test compound; and (iii) determining whether the presence of the compound affects the binding of HLA-E to the cells.

11. The method of claim 10, further comprising using the identified compounds in therapeutic applications, wherein the identified compounds are antibodies.

12. The method of claim 10, wherein the CD94/NKG2 receptor is an inhibitory NK cell receptor.

13. The method of claim 10, wherein the CD94/NKG2 receptor is a stimulatory NK cell receptor.

14. The method of claim 10, wherein the NKG2 member is NKG2A.

15. The method of claim 10, wherein the NKG2 member is NKG2C.

16. The method of claim 10, wherein the test compound is an antibody.

17. A method for screening and producing an identified compound which affects the binding of HLA-E to CD94/NKG2 receptors, which method comprises:

(i) selecting a test compound for screening;

(ii) providing cells expressing a CD94/NKG2 receptor at the cell surface, wherein the NKG2 member is selected from a group consisting of NKG2A, NKG2B, NKG2C, NKG2E, and NKG2F;

(iii) contacting the cells with HLA-E in the presence of the test compound;

(iv) determining whether the presence of the test compound affects the binding of HLA-E to the cells thereby providing an identified compound; and (v) producing the identified compound which affects the binding of HLA-E to the cells.

18. The method of claim 17, wherein the CD94/NKG2 receptor is an inhibitory NK cell receptor.

19. The method of claim 17, wherein the CD94/NKG2 receptor is a stimulatory NK cell receptor.

20. The method of claim 17, wherein the NKG2 member is NKG2A.

21. The method of claim 17, wherein the NKG2 member is NKG2C.

22. The method of claim 17, wherein the test compound is an antibody.

* * * * *

UNITED STATES PATENT AND TRADEMARK OFFICE

CERTIFICATE OF CORRECTION

PATENT NO. : 7,410,767 B1
APPLICATION NO. : 09/555555
DATED : August 12, 2008
INVENTOR(S) : Braud et al.

It is certified that error appears in the above-identified patent and that said Letters Patent is hereby corrected as shown below:

TITLE PAGE ITEM [75]:

The residence city for inventor Veronique M. Braud should be changed from "Oxford" to state --Shrivenham--.

Signed and Sealed this

Eighth Day of June, 2010

David J. Kappos
*Director of the United States Patent and Trademark Office*